United States Patent [19]

Waycaster et al.

[11] 4,370,553
[45] Jan. 25, 1983

[54] CONTAMINATED SAMPLE GAS ANALYZER AND GAS CELL THEREFOR

[75] Inventors: Roy A. Waycaster, Tecumseh; William T. Baker, Ann Arbor; Jerry D. Bidle, Tecumseh, all of Mich.

[73] Assignee: Sensors, Inc., Saline, Mich.

[21] Appl. No.: 165,250

[22] Filed: Jul. 2, 1980

[51] Int. Cl.³ .............................................. G01J 1/04
[52] U.S. Cl. .................................. 250/343; 250/345; 356/246
[58] Field of Search ............... 356/440, 246; 250/343, 250/344, 345, 252; 128/719

[56] References Cited

U.S. PATENT DOCUMENTS

| | | | |
|---|---|---|---|
| 2,258,073 | 10/1941 | Stevens | 356/246 |
| 3,307,447 | 3/1967 | Carleton et al. | 356/246 |
| 3,572,946 | 3/1971 | Little | 356/246 |
| 3,790,797 | 2/1974 | Sternberg et al. | 250/345 |
| 3,927,670 | 12/1975 | Turney et al. | |
| 3,957,372 | 5/1976 | Jowett et al. | 250/345 |
| 3,958,122 | 5/1976 | Jowett et al. | 250/346 |
| 3,973,123 | 8/1976 | Adolph et al. | 250/343 |
| 3,973,848 | 8/1976 | Jowett et al. | 250/345 |
| 3,996,010 | 12/1976 | Fraser | 250/576 |
| 4,008,394 | 2/1977 | Risgin et al. | 250/345 |
| 4,011,859 | 3/1977 | Frankenberger | |
| 4,013,260 | 3/1977 | McClatchie et al. | 250/343 |
| 4,050,823 | 9/1977 | Frankenberger | 250/343 |
| 4,067,320 | 1/1978 | Olsson et al. | 250/373 |
| 4,082,459 | 4/1978 | Wolfe | 250/458 |
| 4,103,174 | 7/1978 | McClatchie et al. | 250/493 |
| 4,157,470 | 6/1979 | Kotaka et al. | 250/345 |
| 4,177,381 | 12/1979 | McClatchie et al. | 250/345 |
| 4,180,734 | 12/1979 | Gedeon | 250/345 |
| 4,220,415 | 9/1980 | Staab et al. | 250/343 |
| 4,266,131 | 5/1981 | Ahjopalo et al. | 250/345 |

OTHER PUBLICATIONS

Nuzzo, "Capnography in Infants and Children", *Respiratory Therapy*, Sep./Oct. 1978, pp. 15-20.

Primary Examiner—Alfred E. Smith
Assistant Examiner—Carolyn E. Fields
Attorney, Agent, or Firm—Price, Heneveld, Huizenga & Cooper

[57] ABSTRACT

A gas analyzer for performing gas analysis on a sample gas containing contaminants which normally interfere with the operation of the analyzer is disclosed comprising a source of radiant energy; means for directing radiant energy through a sample gas; a disposable gas cell; a detector for receiving radiant energy; and a circuit for analyzing the output of the detector and indicating the concentration of predetermined constituents in the sample gas. The gas cell comprises a disposable sample gas cell having a sample enclosure for containing a sample gas volume; sample windows defining a portion of a sample gas optical path extending from the source of radiant energy through the sample gas volume to the detector; an inlet for supplying sample gas to the sample gas volume and an outlet for exhausting sample gas from the sample gas volume. The disposable sample cell is provided with inlet and exhaust manifolds having cross-sectional areas that minimize dead space and insure laminar flow, minimizing stagnant areas. Specifically, the cross-sectional areas of the inlet and outlet manifolds are relatively constant, the cross-sectional area of the outlet being larger than the cross-sectional area of the inlet, and the inlet and outlet manifolds vary in cross-sectional shape from elongate shapes proximate the windows to a shape having roughly equilateral dimensions distal to the windows. The analyzer and the gas cell are provided with a number of inter-related features that make the analyzer self aligning and eliminates the necessity of recalibrating the analyzer each time a sample cell is replaced.

34 Claims, 22 Drawing Figures

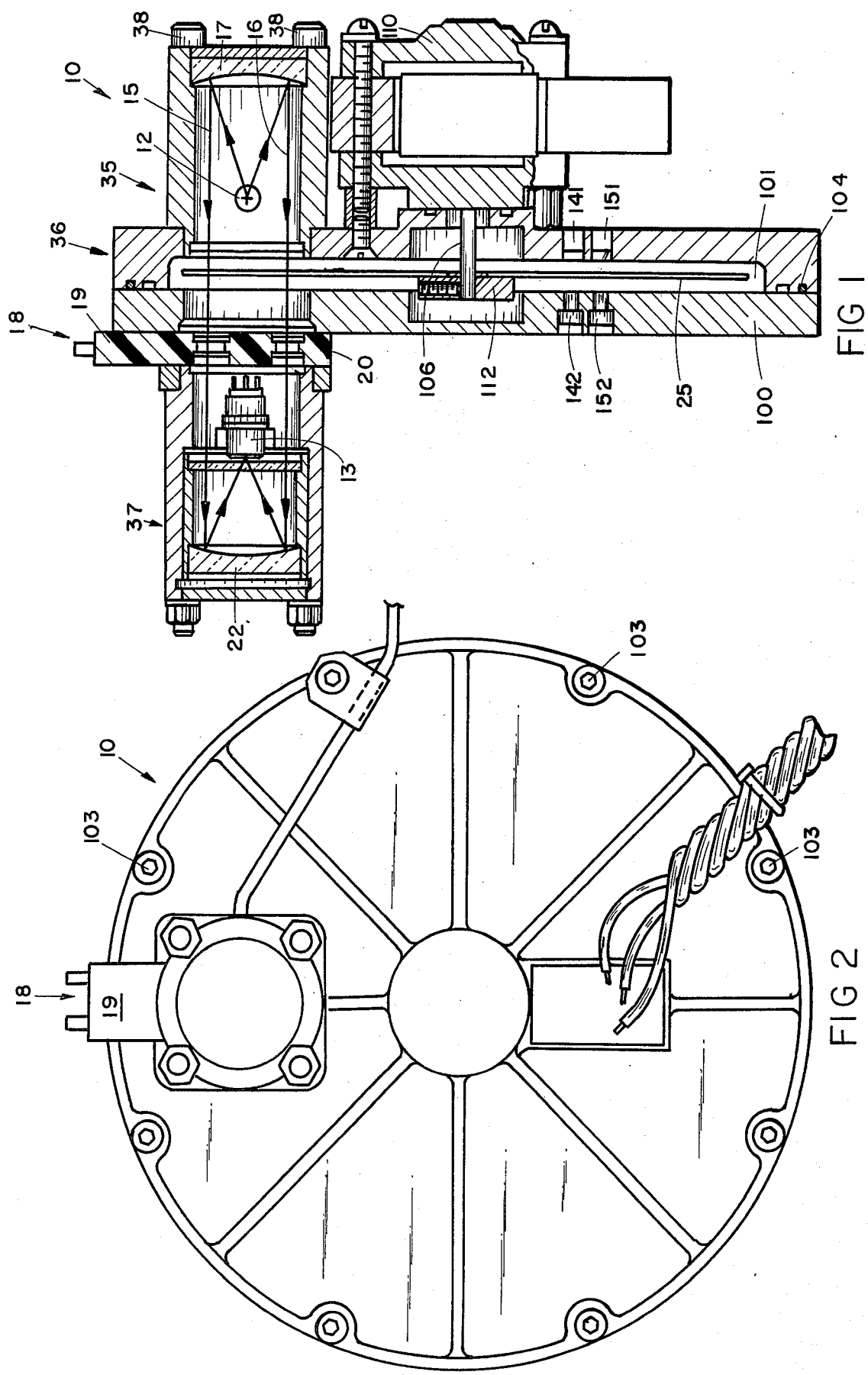

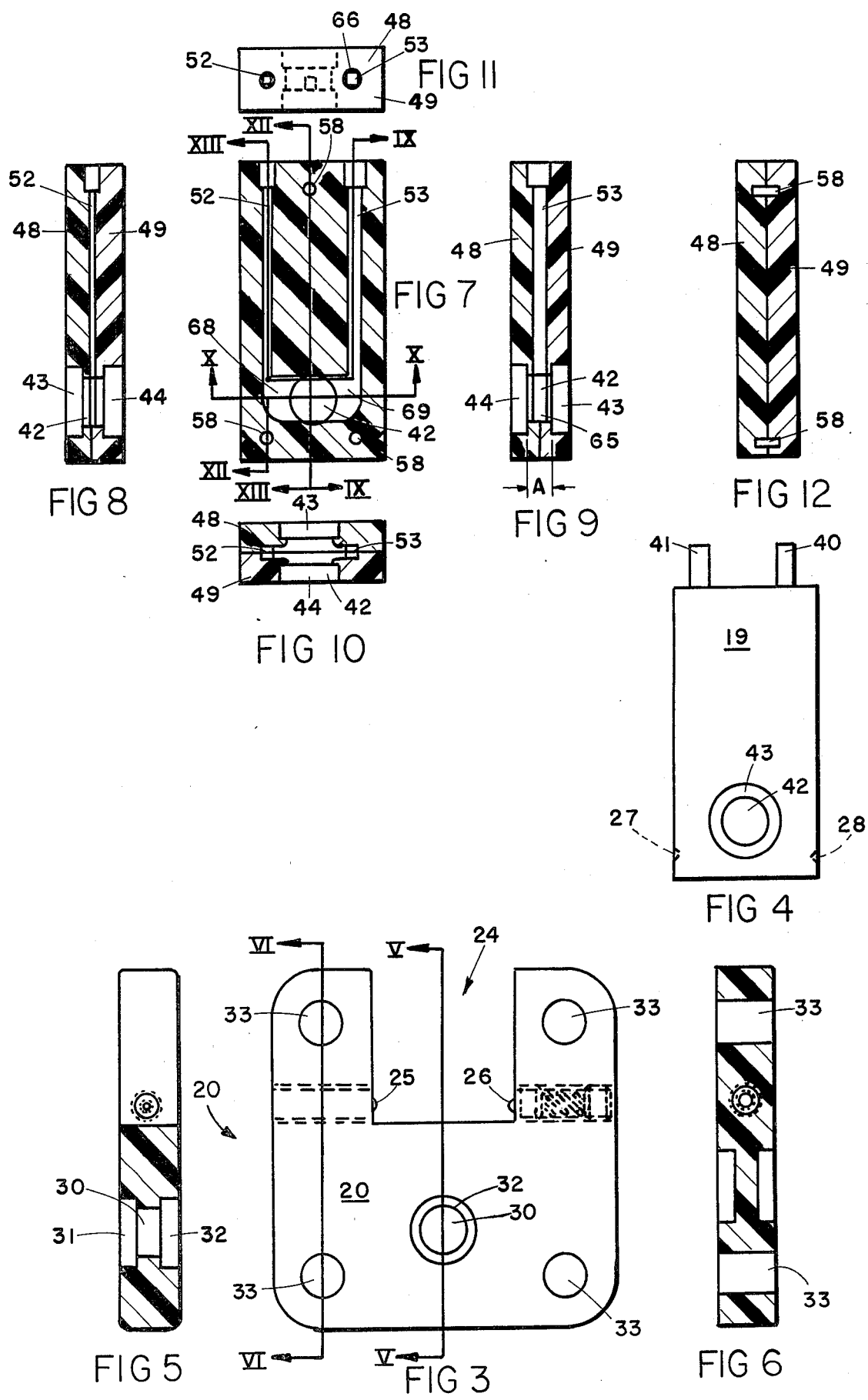

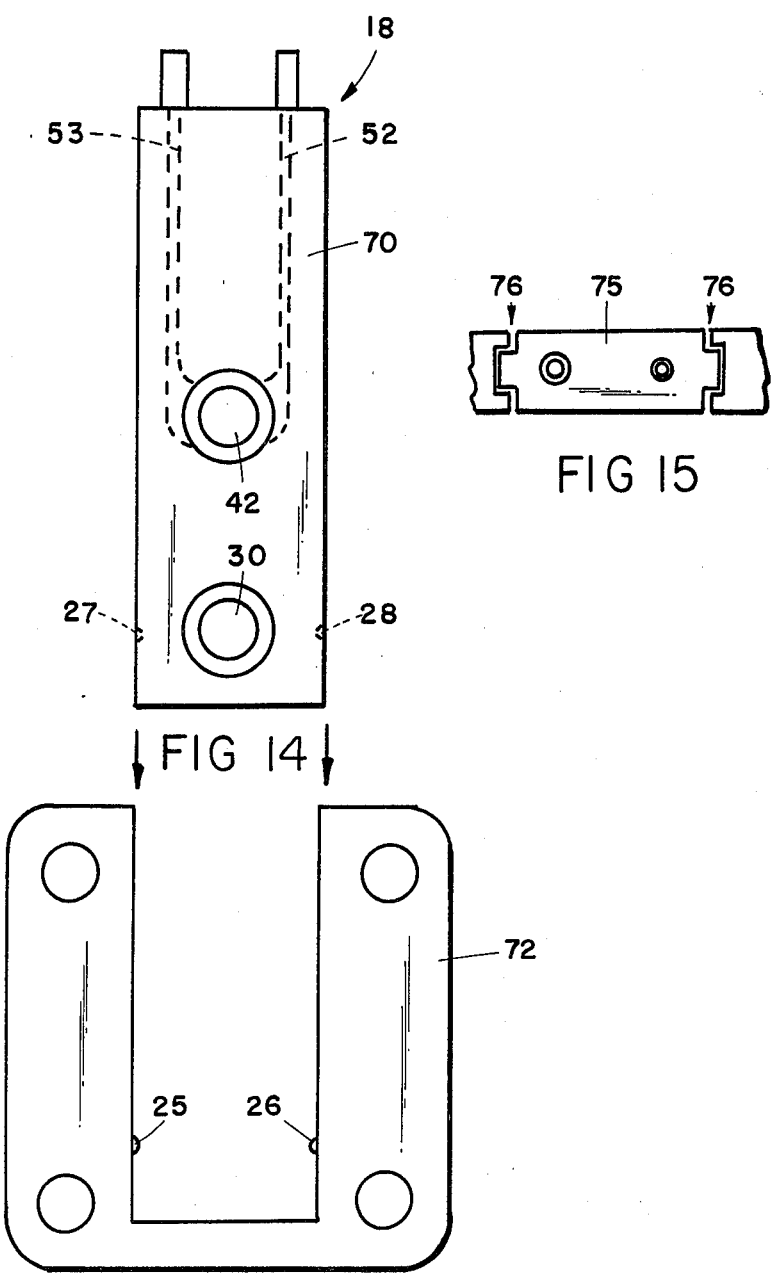

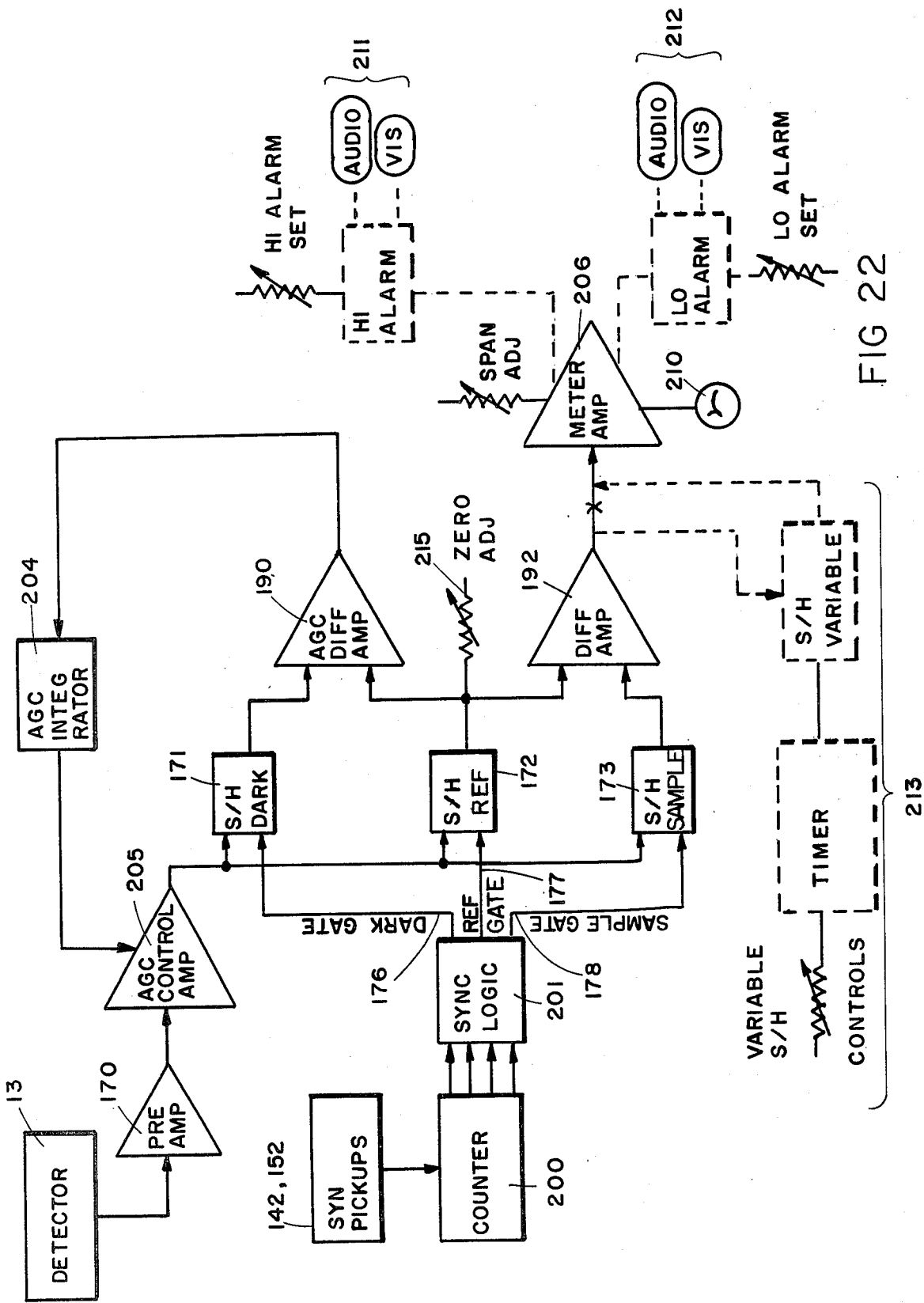

CONTAMINATED SAMPLE GAS ANALYZER AND GAS CELL THEREFOR

BACKGROUND OF THE INVENTION

The present invention relates generally to gas analyzers suitable for use in analyzing a sample gas containing contaminants which normally interfere with the operation of the analyzer and more particularly, is directed to a gas cell for use in such an analyzer.

Both dispersive and non-dispersive radiant energy gas analyzers are used in the prior art to measure certain predetermined constituents of a sample gas which may contain other contaminants which normally interfere with the operation of the analyzer. Applications for non-dispersive type radiant energy gas analyzers that involve measuring constituent gases in a contaminated sample gas involve such diverse applications as breathing gas analysis and determining emission levels in the exhaust of an internal combustion engine. Applications for these types of analyzers in the field of breathing gas analysis include for example the art of capnography, encountered in the medical sciences, and the problem of determining ethanol concentration, encountered in the field of law enforcement.

The art of capnography involves the measurement of carbon dioxide concentrations in breathing gas expelled from a patient's lungs. This data can be useful in determining the patient's ventilatory status and other physiological conditions. The principles of capnography were discovered by K. Luft and were published in 1943 in "Über eine neue Methode der registrietenden Gasanalyse mit Hilfe der Absorbtion ultraroter Strahlen ohne spektrale Zerlegung," Ztschr.I. Techn. Phys. Vol. 24, 1943, p 97.

Other monitoring techniques exist for monitoring a patient's breathing during anesthesia, however, in addition to being informative, to be useful in an operating room these techniques must be non-invasive, easy for the anesthetist to use, require a minimum of equipment adjustment or calibration; and be relatively free of artifacts. Many of these conventional techniques are notable for their subjectiveness and qualitative character. These techniques include auscultation of breath sound through a precordial or esophageal stethoscope, observation of the breathing movements of a patient's chest or a breathing bag, the color of structures such as the lips and nail beds of the patient and the color of blood from a surgical wound. Quantitative techniques for obtaining a measurement of breathing efficiency involve measurement of the oxygen in the gas mixture delivered to the patient and measurement of the volume of gases exchanged in the breathing circuit. Unfortunately, these methods measure only the volumes and concentrations delivered by the anesthesia machine, and not necessarily those actually received by the patient. It is well known that one of the most common accidents in anesthesia is unrecognized discontinuity in the breathing system. Such a discontinuity can be revealed by oximetry which measures the patient's oxygen saturation, however, instruments of satisfactory quality for conducting such an operation are very expensive and the transducer alone is quite bulky. Highly accurate and comprehensive information on both inspired and expired gases are available by mass spectrometry but this method is even more expensive and bulky, and although direct arterial gas analysis provides a sensitive measure of effective ventilation, its invasiveness limits its applicability.

In contrast, a dynamic breath-by-breath $CO_2$ analysis with a non-dispersive radiant energy gas analyzer can present many advantages. This method is a sensitive indicator of the adequacy of breathing because of the close relationship between respiratory depth and partial pressures of $CO_2$ in the arterial blood and in the end expired air. For example, falling $CO_2$ levels in the patient's breath can indicate when ventilation is increased, the production of $CO_2$ is decreased, transport to the lungs is decreased, transport between the lips and alveoli is impeded, a gross depression of respiration occurs, transport between the patient and the analyzer is impeded or when there is an admixture of non-$CO_2$ containing gases. $CO_2$ levels in the patient's expired gases will increase when ventilation is decreased (other than an extreme decrease), production of $CO_2$ is increased, transport to the lungs is increased, there is rebreathing, $NaHCO_3$ is infused or water has entered the analyzing chamber. Although the utility of the method has been recognized for many years, it has not achieved general use because of the limitations of earlier non-dispersive type radiant energy gas analyzers.

Typically, in capnography a non-dispersive infrared gas analyzer is used to measure the concentration of $CO_2$ in a multi-component gas mixture based on the absorption of an infrared beam of a specific wave length by the $CO_2$ in the gas mixture. Infrared absorption by a gas mixture is a characteristic of the type and arrangement of the atoms comprising the gas molecules of the mixture. Various types of gas molecules generally exhibit characteristic absorption spectra that are related to the number, configuration and types of atoms in a given molecule. The simpler the molecular structure, the simpler the absorption spectrum. Conversely, the heavy, more complicated molecules exhibit quite complex spectra. Infrared radiant energy intereacts with the molecules of the gas mixture, the degree of interaction being a function of the spectral absorption bands for the different gas components of the mixture and the number of molecules of absorbing gas of each mixture that are present.

By examining the absorption spectra of the specific gas of interest, one can generally locate an infrared absorption band that is unique to that gas or one that at least would not interact with other gases. Typically, the analyzer compares the infrared transmittance of two identical optical paths. One path passes through a sample cell which is filled with a gas of unknown $CO_2$ concentration and the other path passes through a reference cell which is filled with a reference gas. The spectrum of the infrared beam that is passed through the two cells includes an unique absorption band of the $CO_2$ molecules within the cells. Since the number of gas molecules per unit volume is proportional to the partial pressure of the gas, a measure of the absorption is a direct indication of the partial pressure of the absorbing gas component. The difference in infrared transmittance between the two optical paths is sensed by a detector whose output is a measure of the partial pressure of $CO_2$ in the sample. The electrical impulses or output of the detector can also be relayed to a recorder that records a curve on paper that is representative of $CO_2$ concentration versus time. This curve is known as a capnogram.

Obtaining a representative gas sample of the patient's expired breathing gases is probably the most important consideration and is the source of most potential problems when capnography is attempted. Currently the best way to obtain a sample gas is to modify the breathing head on the ventilator circuit to accept an analyzer sampling line. The sampling catheter should be attached so that it draws from the expired air stream. Other techniques employ an adapter that fits between a ventilator and an endotrachial tube for obtaining a gas sample. A more complete description of the art of capnography may be found in "Capnography In Infants and Children" by Phillip P. Nuzzo, Respiratory Therapy, September October, 1978.

Problems with prior art non-dispersive type $CO_2$ gas analyzers that have prevented their widespread use in the operating room have included inconvenience of operation due to the complexity and bulkiness of the equipment; the difficulty of obtaining representative end-tidal samples from the anesthetized patient (end-tidal refers to the very last portion of the breath exhaled by a patient) especially at small tidal volumes and rapid respiratory rates; instability of the analyzer itself requiring frequent zero adjustment and recalibration; the high incidence of artifacts due for example, to interference from $N_2O$, electrocautery and particulate matter such as water, blood or mucous in the sample cell; and lastly, the high cost of the analyzing equipment.

SUMMARY OF THE INVENTION

According to the present invention, these and other problems in the prior art are solved by provision of a gas analyzer and gas cell therefor for performing gas analysis on a sample gas containing contaminants. The gas analyzer comprises a source of radiant energy; means for directing radiant energy through a sample gas, the radiant energy being directed along a sample gas optical path; detector means for receiving radiant energy from the sample gas optical path; and circuit means for analyzing the output of the detector and indicating the concentration of predetermined constituents of the sample gas. A gas cell is disposed in the sample gas optical path comprising a disposable sample gas cell having a sample enclosure for containing a sample gas volume. The disposable gas cell further includes a sample window means for defining a portion of the sample gas optical path extending through the sample gas volume, an inlet for supplying sample gas to the sample gas volume, and an outlet for exhausting sample gas from the sample gas volume. The disposability of the gas cell eliminates contamination of the cell as a major problem with these types of analyzers since when the cell is contaminated with mucous, blood or the like, it is easily removed and inexpensive to replace.

According to more narrow aspects of the invention, stagnant air and dead space is reduced by providing a sample gas cell featuring transverse gas flow and an inlet manifold interconnecting the inlet of the cell and the sample gas volume. The inlet manifold is provided with a cross-sectional area that remains constant between the inlet of the cell and the sample volume. While the cross-sectional area of the inlet manifold remains constant, the shape of the cross-sectional area of the inlet manifold varies gradually from a shape having roughly equilateral dimensions at the inlet of the cell to a narrow shape defining a uniform short cell path length at the sample volume. The cell further includes an exhaust manifold having a gradually increasing cross-sectional area extending from the exit of the sample volume. This construction along with provision of a relatively small sample volume eliminates dead space, facilitates laminar flow which minimizes stagnant areas, increases response time, insures an accurate end-tidal volume and helps eliminate the need for constant recalibration when changing gas cells.

According to more narrow aspects of the invention, the gas analyzer comprising a dual beam non-dispersive infrared gas analyzer having a single source of infrared energy and a single detector. The gas cell further includes a reference gas cell containing a volume of reference gas and a reference window means for defining a portion of a reference gas optical path therethrough. A dual beam analysis is achieved by provision of a rotating chopper wheel containing reference windows and sample windows for alternately directing infrared energy through the reference gas and sample gas optical paths, respectively. The chopper wheel further includes a dark window which blocks the passage of radiant energy through either of the reference gas or sample gas optical paths. Gating circuitry, sample/hold circuitry, automatic gain control circuitry and differential amplifiers are used to first determine the difference between the reference and dark output of the detector and hold this difference constant. Then the same output of the detector is subtracted from the reference output of the detector to provide an accurate measure of the $CO_2$ concentration in the sample gas corrected for detector drift due to ambient temperature conditions. This substantially shortens the required warmup period for the analyzer and eliminates many calibration problems. Other features of the analyzer that improve its accuracy and reliability involve the use of negative cells filled with interfering gases frequently found in the sample gas, disposing the detector septum, and source mounting struts in a roughly parallel relationship between the sample and reference cells, centering the infrared source to the side of the focal point of a mirror that generates a collimated beam of infrared energy to compensate for thermal expansion of the source, along with the overall modular construction of the unit which in itself facilitates alignment.

BRIEF DESCRIPTION OF THE DRAWINGS

FIG. 1 is a side elevational view partially in section of the optical bench assembly of the analyzer of the present invention.

FIG. 2 is a front elevational view of the optical bench assembly of the analyzer of the present invention.

FIG. 3 is a front elevational view of the reference cell of the present invention.

FIG. 4 is a front elevational view of the sample cell of the present invention.

FIG. 5 is a sectional view of the reference cell of the present invention taken along line V—V of FIG. 3.

FIG. 6 is a sectional view of the reference cell of the present invention taken along line VI—VI of FIG. 3.

FIG. 7 is a section of the front elevation of the sample cell of the present invention.

FIG. 8 is a sectional view of the sample cell of the present invention taken along line VIII—VIII of FIG. 7.

FIG. 9 is a sectional view of the sample cell of the present invention taken along IX—IX of FIG. 7.

FIG. 10 is a sectional view of the sample cell of the present invention taken along line X—X of FIG. 7.

FIG. 11 is a top view of the sample cell of the present invention.

FIG. 12 is a sectional view of the sample cell of the present invention taken along line XII—XII of FIG. 7.

FIG. 13 is a front elevational view of a portion of a gas cell constructed according to the present invention.

FIG. 14 is a front elevational view of a combination disposable sample and reference cell constructed according to the present invention.

FIG. 15 is a partial top view of the disposable section and fixed sections of a gas cell constructed according to the present invention illustrating a labrynith seal that extends between the fixed and disposable gas cell sections.

FIG. 22 is a schematic illustration of a circuit that is used to analyze the output of the detector according to the present invention.

DESCRIPTION OF THE PREFERRED EMBODIMENTS

Figure 18:
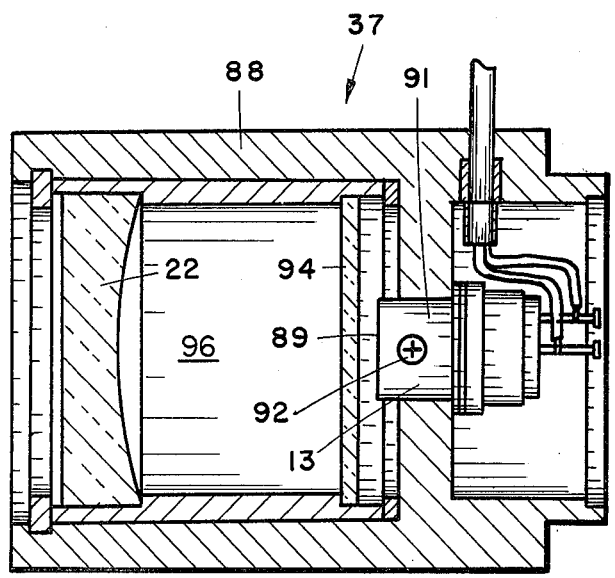
FIG. 18 is a sectional side elevational view of the detector subassembly of the present invention.

Referring now to FIGS. 1 and 2, an optical bench assembly for a non-dispersive infrared gas analyzer is illustrated at 10. The optical bench assembly 10 is normally mounted within a suitable housing, not illustrated herein, which protects the bench assembly from environmental debris and also houses other components of the analyzer such as an output meter, high and low level alarms, a power supply and circuits for analyzing the output of the detector. In the present embodiment, the analyzer is particularly adapted for use in capnography and is ideally suited for monitoring endtidal $CO_2$ concentrations in the breathing gases of an anesthesized patient. However, it should be understood that the gas analyzer of the present invention may have utility performing gas analysis on a wide variety of sample gases containing contaminants which normally interfere with the operation of the analyzer. Preferably, the analyzer is a dual beam, non-dispersive infrared analyzer including a single source of infrared energy at 12 and a suitable detector at 13. In the present case a lead selenide detector is preferred, however, other types of detectors, such as thermopile detectors may be suitable. It should also be understood that depending on the application, sources of radiant energy other than that of the infrared spectrum and suitable detectors for detecting these sources of radiant energy may be employed. The analyzer further includes means for directing radiant energy along a sample gas optical path 15 and a reference gas optical path 16 comprising a concave mirror 17 having a focal point disposed approximately at the center of the infrared source 12. The infrared source 12 and mirror 17 produce a collimated beam of infrared energy that is projected through a gas cell generally indicated by the numeral 18. In the case of a dual beam analyzer, the gas cell 18 will include a sample gas cell 19 and a reference gas cell 20. In single beam analyzers, only the sample cell portion 19 is required. The detector 13 receives radiant energy from the sample gas path 15 and the reference gas path 16 reflected from concave mirror 22 having a focal point approximately centered on the face of the detector 13. The optical bench assembly 10 of the dual beam analyzer further includes a rotating chopper wheel 25 having windows for alternately directing infrared energy through one of the sample cell and reference cells. The analyzer further includes circuit means, not illustrated in FIG. 1, for analyzing the output of the detector 13 and providing an indication of the concentration of predetermined constituents of the sample gas. The theory and operation of non-dispersive dual beam comparison gas analyzers using a single source and single detector of radiant energy with a single chopper disc disposed therebetween, is disclosed in further detail in prior U.S. Pat. No. 4,008,394 to Risgin et al, the disclosure of which is hereby incorporated by reference. Use of a single source and a single detector of radiant energy with a chopper wheel disposed therebetween for alternately directing radiant energy through a sample gas and a reference gas provide a gas analyzer having inherently fast response times while providing an accurate radiation absorption comparison type gas analysis. This type of analyzer solves many of the problems inherently present in matching detectors, optical paths, and thermally balancing infrared sources in other types of dual beam, non-dispersive gas analyzers. It should also be understood that like the gas analyzer taught by Risgin et al a multiple gas analysis may be achieved by providing a plurality of optical assemblies, each having a separate source, gas cell and detector, the optical assemblies being radially spaced about the chopper wheel 25.

In this case, the sample cell 19 is a disposable unit slidably received within the reference cell 20 which is fixed within the optical bench assembly 10. However, as hereinafter illustrated, the reference cell 20 as well as the sample cell 19 may be disposable.

With reference now to FIGS. 3 and 4, the sample cell 19 and reference cell 20 are illustrated in further detail. The reference cell 20 includes means for removably mounting the disposable sample gas cell 19 comprising a channel 24 for slidably receiving the sample cell 19. In this case the reference cell 20 can be regarded as a connector module that permits removal of the sample cell 19 without disturbing the sample and reference gas optical paths. The channel 24 includes spring clip means comprising a pair of spring biased ball bearings 25 and 26 projecting from opposing sides of the channel 24. The spring loaded ball bearings 25 and 26 are biased into engagement with the sides of the sample cell 19 and the sample cell 19 includes first and second ball engaging seats 27 and 28. When the reference cell 20 is bolted into the optical bench assembly 10, the channel 24 in the reference cell 20 defines a slot into which the sample cell 19 is pushed. The operator, when inserting a sample cell 19, simply slides the cell downwardly into the slot defined by the channel 24 and abutting surfaces of the optical bench assembly until resistance from the ball bearings 25 and 26 is felt. Thereafter, the operator pushes downwardly with sufficient force to cam the ball bearings inwardly and when the sample cell 19 is fully seated within the reference cell 20, the ball bearings 25, 26 snap into the ball bearing engaging seats 27 and 28, respectively, to properly orient and mount the sample cell 19 in the sample gas optical path.

The reference cell 20 includes a reference gas volume 30, best illustrated in FIG. 5, bounded by infrared transparent windows 31 and 32. The reference gas volume 30 is normally filled with a suitable gas such as ambient air. The reference volume 30 is hermetically sealed when the windows 31 and 32 are cemented or otherwise suitably bonded to opposing sides of the reference volume. The reference portion 20 of the cell 18 further includes means for fixedly securing the same to the optical bench assembly comprising a plurality of apertures 33. As best illustrated in FIG. 1, the optical bench assembly comprises a plurality of subassemblies, including a source subassembly 35, a chopper wheel subassembly 36, the cell 18 and a detector subassembly 37. The apertures 33 in the reference portion 20 of the cell 18 receive through mounting bolts 38 which extend through each of the aforementioned subassemblies to automatically optically align the same and clamp the subassemblies theretogether.

Referring to FIG. 4, the sample cell 19 is illustrated in further detail. The sample cell 19 includes an inlet 40 and an outlet 41 supplying sample gas to a sample volume 42 bounded by windows 43 and 44, best illustrated in FIGS. 8, 9 and 10. Preferably, both the sample cell 19 and reference cell 20 are injection molded parts formed from a polymeric material and the sample cell inlet and outlet 40 and 41 are preferably metal tubes suitably bonded to the sample cell 19. The exhaust or outlet tube 41 may be vented to the atmosphere. The inlet tube 40 will be connected to a sampling catheter suitably placed in the patient's breathing circuit for obtaining a representative sample of the patient's end-tidal gases.

With further reference to FIGS. 7 through 12, it is illustrated that the sample cell 19 is formed from first and second substantially identical halves 48 and 49. The substantially identical halves 48 and 49 each include half of a sample enclosure including half of the sample volume 42, one of the sample windows 43 and 44 bounding the sample volume 42, half of an inlet manifold 52, and an exhaust manifold 53. The first and second halves 48 and 49 are suitably bonded together with an adhesive or by ultrasonic welding to define the sample volume, the inlet manifold and exhaust manifold therebetween. As best illustrated in FIGS. 7 and 12, each of the first and second halves 48 and 49 are provided with apertures for receiving a plurality of locator pins 58. The inlet manifold 52 interconnects the inlet tube 40, not illustrated in FIGS. 7 through 12 and the sample volume 42. The exhaust manifold 53 interconnects the exhaust tube 41, not illustrated in FIGS. 7 through 12, and the sample volume 42. The inlet and exhaust manifolds are arranged to provide a flow pattern in the sample volume 42 that extends transversely to the sample gas optical path 15, illustrated in FIG. 1. In other embodiments of the invention the molded halves 48 and 49 may be replaced by a single piece sample cell body.

The sample volume 42 is a relatively small volume defined on opposing sides by windows 43 and 44. Preferably, the cell length A, best illustrated in FIG. 9, defined between opposing windows 43 and 44 is on the order of one millimeter. This, taken along with the specific cross-sectional areas and shapes provided in the inlet and exhaust manifolds minimizes dead space and insures laminar flow, eliminating stagnant areas in the sample cell 19. More specifically, the inlet manifold 52 is provided with a constant cross-sectional area extending from the inlet tube 40 to the sample volume 42. The cross-sectional area chosen for the inlet manifold 52 is preferably approximately equal to the cross-sectional area of the inlet tube 40. Although the cross-sectional area of the inlet manifold 52 remains constant, the shape of the cross-sectional area of the inlet manifold 52 varies from a shape having roughly equilateral dimensions at the inlet tube 40 to an elongate shape having a uniform width measured at the smallest dimension of the shape as it enters the sample volume. Preferably, the shape of the inlet manifold at the inlet tube 40 is square, as best illustrated in FIG. 11. However, at the entrance of the sample volume 42, the cross-sectional shape of the inlet manifold 52 is an elongate rectangle, best illustrated in FIG. 8, extending parallel to, and bounded by the windows 43 and 44.

The exhaust manifold 53 is provided with a relatively constant cross-sectional area approximately equal to the cross-sectional area of the exhaust tube 41 and substantially larger than the cross-sectional area of the inlet manifold 52. This arrangement minimizes back pressure in the sample cell 19. Although the cross-sectional area of the exhaust manifold 53 remains substantially constant, the cross-sectional shape of the exhaust manifold 53 varies from that of an elongate rectangle bounded by the windows 43 and 44 at 65 to that of a square at the exhaust tube 41, best illustrated at 66 in FIG. 11. Both the inlet manifold 52 and the exhaust manifold 53 contain sweeping 90° turns at 68 and 69 so that the inlet and outlet tubes 40 and 41 are conveniently placed at the top of the optical bench assembly 10, best illustrated in FIG. 1, to facilitate the mounting of connecting hoses.

With brief reference now to FIGS. 13 and 14, an embodiment of the gas cell 18 is illustrated having a disposable sample and reference cell 70. In this case, both the sample volume 42 and the reference volume 30 are incorporated in a combination disposable sample and reference cell 70 formed from first and second injection molded halves defining the inlet manifold 52, the exhaust manifold 53, the reference volume 30 and the sample volume 42. The design of the disposable combination sample and reference cell is essentially the same as the disposable sample cell previously illustrated, except that the cell 70 is somewhat longer and also incorporates the reference volume 30. The cell 70 includes seats 27 and 28 for engaging spring loaded ball bearings 25 and 26 to securely mount the cell 70 in a mounting plate 72, bolted into the optical bench assembly 10 in the manner previously described.

With reference to FIG. 15, it is illustrated that in some embodiments of the invention, the disposable portion 75 of the gas cell may be provided with a suitably shaped labyrinth seal extending about its periphery. The labyrinth seal 76 minimizes light leakage and acts as a track for guiding the disposable portion 75 of the cell during insertion. Preferably, both the disposable and fixed portions of the gas cell are formed from the same material to eliminate problems associated with differential rates of thermal expansion.

Figure 17:
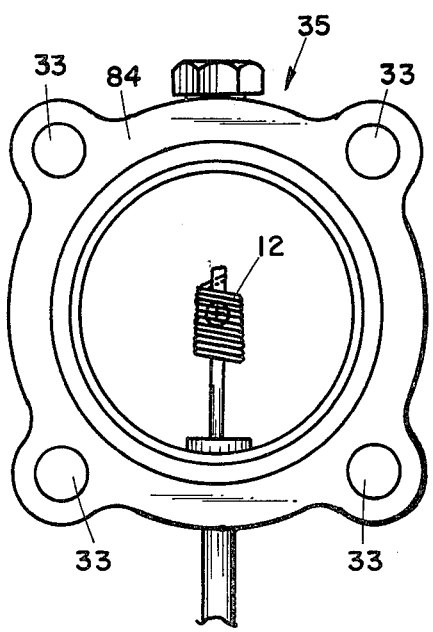
FIG. 17 is a front elevational view of the source subassembly of the present invention.
Figure 16:
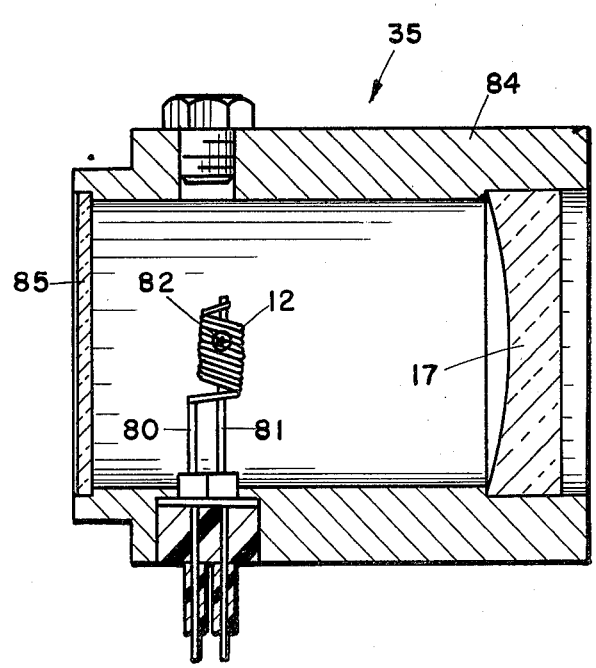
FIG. 16 is a sectional side elevational view of the source subassembly of the present invention.

With reference to FIGS. 16 and 17, as well as FIG. 1, the source subassembly 35 is illustrated in further detail. The source of infrared radiation 12 comprises a coil of electrical resistance heated wire mounted on a pair of electrically conductive struts 80 and 81. Preferably, the source 12 is centered just to the side of the focal point 82 of the mirror 17 to insure that several coils of the electrically heated source 12 are always disposed at the focal point 82 of the mirror 17 as the coil grows due to thermal expansion. The mirror 17, housing 84, and window 85 define a hermetically sealed cavity for the source 12 that is backfilled with a suitable gas such as argon or nitrogen. The mirror 17 projects a collimated beam of infrared energy toward the window 85. The housing 84 is provided with a plurality of apertures 33 for receiving through bolts 38 of optical bench assembly 10 and automatically optically aligning the source subassembly 35 with the remaining subassemblies of the optical bench assembly.

Figure 19:
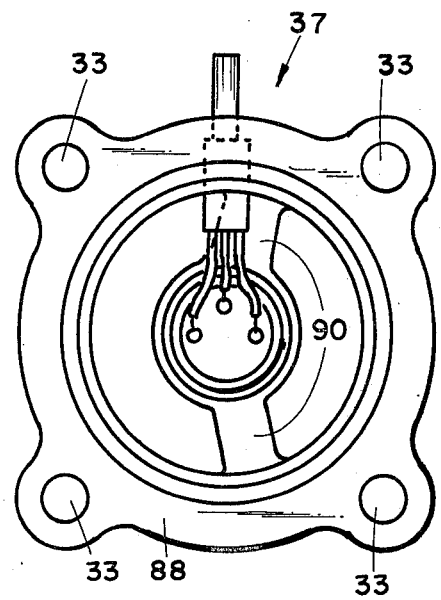
FIG. 19 is a front elevational view of the detector subassembly of the present invention.

With reference now to FIGS. 18 and 19, as well as FIG. 1, the detector subassembly 37 of the present invention is illustrated in further detail. Preferably, the detector 13 comprises a lead selenide detector having a filter, not illustrated herein, epoxied or otherwise suitably secured to the face 89 of the detector. In the case of a breath-by-breath CO2 monitor, the filter will be provided with a suitable CO2 absorption band, for example, the filter may be provided with a center wave length of 4.26 microns plus one half percent, minus one percent. The housing 88 is provided with a septum 90 having a central aperture 91 into which the detector 13 is pressed. A concave mirror 22 receives radiant energy from the sample gas and reference gas optical paths and reflects the same to the detector 13 which is approximately centered on the focal point 92 of the mirror 22. The detector housing 88, mirror 22, and window 94 define a cavity 96 which is filled with interfering gases to form a negative cell. For example, in the case of a CO2 monitor, the cavity 96 is filled with nitrous oxide. Nitrous oxide exhibits infrared absorption characteristics similar enough to that of CO2 to create erroneous readings when sufficient quantities of nitrous oxide are contained in the patient's breath gas. Since both the sample gas and reference gas optical paths extend through the negative cell 96, all infrared energy normally absorbed by nitrous oxide is blocked thereby eliminating the effect of the interfering gas on the output of the detector 13. The septum 90 in which the detector 13 is mounted preferably extends between the sample cell 19 and the reference cell 20 and extends generally parallel to the struts 81 upon which the source 12 is mounted. This prevents the struts 80 and 81 or the septum 90 from interfering with the sample gas or reference gas optical paths. The detector housing 88 further includes a plurality of apertures 33 for receiving through bolts 38 and automatically aligning the detector subassembly 37 with the remaining subassemblies of the optical bench assembly.

Figure 20:
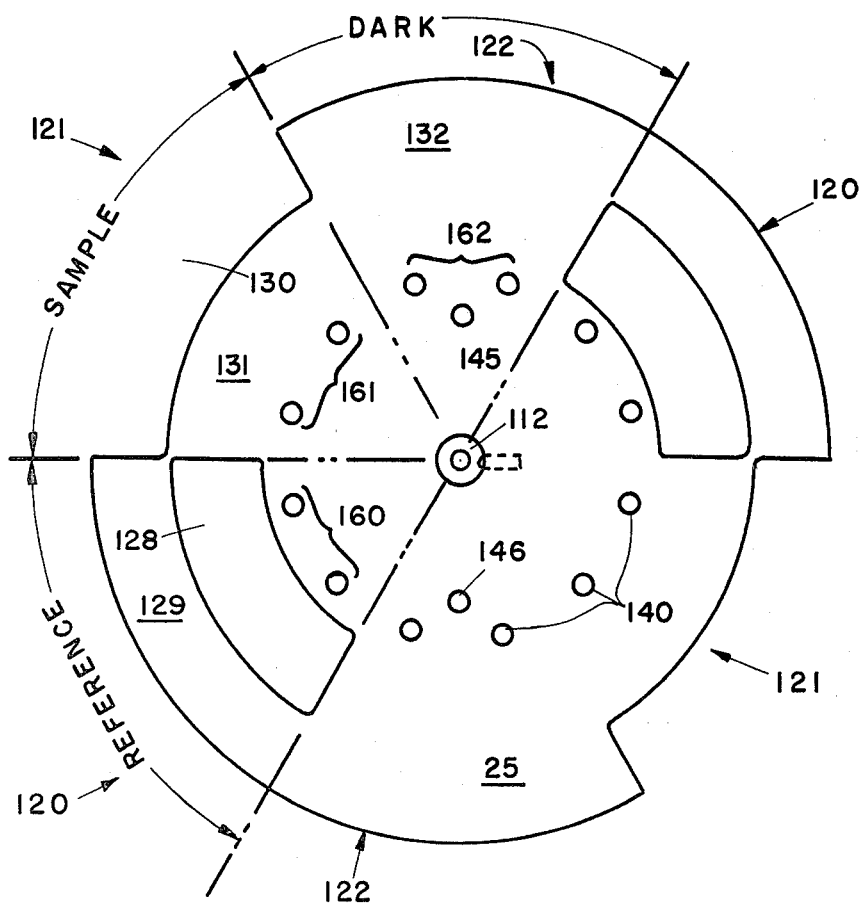
FIG. 20 is an elevational view of the chopper wheel of the present invention.

With reference now to FIG. 20 and FIG. 1, the chopper wheel 25 is illustrated in further detail. The chopper wheel 25 is mounted within a chopper wheel subassembly that contains a housing 100. The housing 100 is comprised of first and second halves defining a cavity 101 in which the chopper wheel 25 runs. The first and second halves of the chopper housing 100 are bolted together at 103. The chopper wheel cavity 101 is hermetically sealed by an O-ring 104 disposed between the halves of the chopper housing 100. A suitable motor shaft seal is also provided to seal the penetration required for motor shaft 106. Preferably, the motor 110 is mounted to the exterior of one of the halves of the chopper housing 100 and comprises a synchronous electric motor. The chopper wheel 25 is bonded to a hub 112 which is provided with a set screw or other suitable means for securing the hub 112 to the motor shaft 106. The chopper wheel 25 rotates at a predetermined relatively constant frequency. The chopper wheel extends between the source 12 and detector 13 in the sample gas and reference gas optical paths 15 and 16, respectively. The chopper wheel 25 is provided with a reference gas section or window 120; a sample gas section or window 121; and a dark section or window 122. The reference window 120 contains an aperture 128 for passing radiant energy extending or passing along the reference gas optical path. The portion 129 of the reference window 120 blocks all radiant energy passing along the sample gas optical path. The sample window 121 contains an aperture 130 that passes radiant energy through the sample gas optical path and includes a portion 131 that blocks all radiant energy in the reference gas optical path. The dark window 122 is provided with a portion 132 that blocks all radiant energy in both the sample gas and reference gas optical paths. In this case, the chopper wheel 25 contains two reference windows, sample windows and dark windows sequentially arranged on opposing sides of the chopper wheel 25. The chopper wheel 25 also includes a plurality of of sync marks or apertures 140. The sync apertures 140 cooperate with a light source 141 and optical pickup 142 mounted in the chopper housing 100 to create gate signals that identify the reference sample and dark windows. A pair of sync reset marks or apertures are disposed on opposing sides of the chopper wheel 25 at 145 and 146. The sync reset apertures 145 and 146 are set 180° apart on the chopper wheel 25 and cooperate with a second light source 151 and a second light detector 152 disposed in the chopper housing 100 to generate a sync reset pulse.

Figure 21:
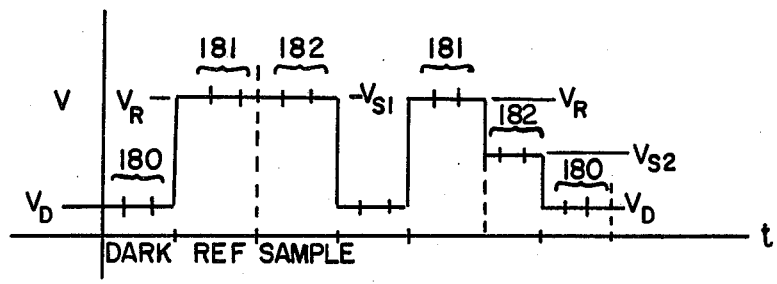
FIG. 21 is a plot of detector output versus time for the gas analyzer of the present invention.

With reference to FIG. 21, a plot of the output of the detector versus time is illustrated. When the dark window 122 is disposed between the detector and the source, the voltage $V_D$ is representative of the portion of the detector output that is a function of noise and ambient temperature. When the reference window 120 extends between the source and detector, the reference gas optical path is open and the voltage $V_R$ represents the output of the detector resulting from infrared energy passing through the reference gas as well as the portion of the detector output representative of noise and ambient temperature. When the sample window 121 is disposed between the source and the detector, an output $V_S$ is provided that is representative of the amount of radiant energy passing through the sample as well as the output of the detector resulting from noise and ambient temperature. $V_{S1}$ in FIG. 21 illustrates the expected output of the detector in the case where the concentration of $CO_2$ in the sample gas is identical to the concentration of $CO_2$ in the reference gas. $V_{S2}$ in FIG. 21 represents the case where the concentration of $CO_2$ in the sample gas is substantially greater than the concentration of $CO_2$ in the reference gas. In this case, less radiant energy is transmitted through the sample gas and the sample gas optical path resulting in a decreased detector output during the period when the sample window 121 extends between the source and detector. The sync pulses generated by the apertures 140 and the optical detector 142 are used to generate gating pulses for identifying each of the dark reference and sample sections of the output of the detector. More specifically, it is illustrated that each of the reference sample and dark sections is provided with a pair of sync apertures 160, 161, and 162, respectively for indicating when the reference sample and dark windows extend between the source and detector. The gating signals generated by these apertures and associated gating circuitry indicate when to sample the output of the detector to obtain dark, reference and sample signals.

With reference now to FIG. 22, the processing strategy of the detector output will be described. FIG. 22 is a schematic of the circuits necessary for processing the output of the detector. After the output of the detector is suitably amplified at 170, it is connected to a dark sample/hold circuit 171, a reference sample/hold circuit 172, and a sample sample/hold circuit 173. A dark gate signal, a reference gate signal and a sample gate signal are received by the dark reference and sample sample/hold circuits 171 through 173 on lines 176 through 178, respectively. The gate signals are generated by the optical detectors 142 and 152, counter 200 and sync logic circuit 201. The gate signals received on lines 176 through 178 sequentially enable and clear each of the dark, reference and sample sample/hold circuits. This allows each of the dark, reference and sample sample/hold circuits to pick off the output of the detector 13 at the points 180, 181 and 182, illustrated in FIG. 21. The gate signals may have a number of formats. If a pair of spaced pulses are provided the first pulse enables the sample/hold circuit and the second pulse clears the sample/hold circuit. In the case of a sample/hold circuit having a predetermined holding period, a single gate pulse may be used. During the period of time extending between the pulses, or during the predetermined holding period of the circuit, the sample/hold circuit will hold the output of the detector. The output of the dark sample/hold circuit 171 and the reference sample/hold circuit 172 are inputted to a first differential amplifier 190. In this way the portion of the output of the detector 13 that is a function of background noise and ambient temperature is subtracted from the reference portion of the output of the detector. Thereafter, the output of first differential amplifier 190 inputted to an automatic gain control circuit. The automatic gain control (AGC) circuit includes an AGC integrator 204 and an AGC control amplifier at 205. The output of the first differential amplifier 190 is inputted to the AGC integrator and the AGC control amplifier 204 and 205 sequentially. The AGC control amplifier is disposed between preamplifier 170 and the inputs of the dark, reference and sample sample/hold circuits. In this manner, the sensitivity of the detector is in effect measured by looking at the output of the detector in its two extreme conditions. First, when the detector receives no radiant energy at all, and the second where the detector receives maximum of radiant energy. This difference is taken and held constant by the AGC circuit. Thereafter, the second differential amplifier 192 takes the difference of the reference and sample signals outputted from reference and sample sample/hold circuits 172 and 173. The output of second differential amplifier 192 is inputted to a meter amplifier 206. The meter amplifier 206 is used to directly drive a $CO_2$ concentration indicating meter 210. The output of the meter amplifier 206 may also be used to trip a high alarm circuit at 211 or a low alarm circuit at 212. Suitable sample/hold variating circuits may be disposed between differential amplifier 192 and meter amplifier 206 as illustrated in 213. Means for zero adjusting and balancing the outputs of the reference and the sample sample/hold circuits is disposed at 215.

The above description should be considered as exemplary and that of the preferred embodiment only. The true spirit and scope of the present invention should be determined by reference to the appended claims. It is desired to include within the appended claims all modifications of the invention that come within the proper scope of the invention.

The embodiments of the invention in which an exclusive property or privilege is claimed are defined as follows:

1. A gas analyzer for performing gas analysis on a sample gas containing contaminants comprising:
   a source of radiant energy;
   means for directing radiant energy through a sample gas, the radiant energy being directed along a sample gas optical path;
   a gas cell comprising a sample gas cell having a sample enclosure for containing a sample gas volume, a sample window means for defining a portion of said sample gas optical path extending through said sample gas volume, an inlet for supplying sample gas to said sample gas volume and an outlet for exhausting sample gas from said sample gas volume, said sample cell being provided with a flow pattern extending transversely with respect to said sample gas optical path, said flow pattern being defined by an inlet manifold interconnecting said inlet and said sample gas volume, said inlet manifold being provided with a roughly constant cross-sectional area, and an outlet manifold extending from said sample gas volume to said outlet, said outlet manifold being provided with a roughly constant cross-sectional area, the cross-sectional area of said outlet manifold being greater than the cross-sectional area of said inlet manifold, the cross-sectional area of said inlet manifold being provided with a shape having roughly equilateral dimensions at said inlet to an elongate shape having a roughly uniform width at said sample volume, and the cross-sectional area of said outlet manifold being provided with an elongate shape having a roughly uniform width at said sample volume to a shape having roughly equilateral dimensions at said outlet, whereby turbulent flow and dead space in said sample gas volume is minimized;
   a connector module for defining a channel for slidably receiving said gas cell and to provide for the periodic removal and replacement of said gas cell while maintaining the optical alignment of the gas analyzer;
   detector means for receiving radiant energy from said sample gas optical path;
   means for securing together in optical alignment said source, said means for directing radiant energy, said connector module and said detector; and
   circuit means for analyzing the output of said detector and indicating the concentration of predetermined constituents of the sample gas.

2. The gas analyzer of claim 1 wherein said means for directing radiant energy also directs radiant energy through a reference gas along a reference gas optical path; said analyzer further includes a reference gas cell comprising a reference cell enclosure for containing a volume of reference gas and a reference window means for defining a portion of said reference gas optical path; said detector means receives radiant energy from said sample gas optical path and said reference gas optical path; and said circuit means indicates the concentration of predetermined constituents of the sample gas by measuring the difference in the amount of radiant energy absorbed by said sample gas and said reference gas.

3. The gas analyzer of claim 2 wherein first and second spring biased detents are provided for engaging opposing sides of said sample cell.

4. The gas analyzer of claim 3 wherein said first and second spring biased detents comprise first and second ball bearings spring biased into engagement with said sample cell; and first and second ball receiving seats disposed on opposing sides of said sample cell for receiving said first and second ball bearings, respectively, and thus properly orienting said sample gas cell in said sample gas optical path.

5. The gas analyzer of claim 2 wherein said gas cell comprises a single unit including said sample gas cell and said reference gas cell.

6. The gas analyzer of claim 2 wherein said sample gas cell and said reference gas cell are formed from the same material.

7. The gas analyzer of claim 2 wherein said source comprises an electrically heated element disposed at approximately the focal point of a concave source mirror, said source mirror comprising said means for directing radiant energy, said source mirror projecting a collimated beam of infrared energy along said sample gas and said reference gas optical paths.

8. The gas analyzer of claim 7 wherein said electrically heated element is disposed in a chamber filled with one of the group of gases consisting of argon and nitrogen.

9. The gas analyzer of claim 7 wherein said electrically heated element is mounted on a plurality of struts.

10. The gas analyzer of claim 9 wherein said detector is mounted on a septum extending roughly parallel to said plurality of struts and between said sample gas and said reference gas optical paths.

11. The gas analyzer of claim 9 wherein said electrically heated element comprises a plurality of electrically heated wire coils centered to the side of said focal point such that as said element is heated it expands through said focal point.

12. The gas analyzer of claim 2 wherein said means for directing radiant energy includes a chopper wheel disposed between said source and said detector in said sample gas and said reference gas optical paths.

13. The gas analyzer of claim 12 wherein said chopper wheel is driven by a synchronous electric motor.

14. The gas analyzer of claim 12 wherein said chopper wheel comprises a reference window, a sample window and a dark window.

15. The gas analyzer of claim 14 wherein said reference window blocks said sample gas optical path and is open in sad reference gas optical path providing for the passage of radiant energy therethrough; said sample window blocks said reference gas optical path and is open in said sample gas optical path providing for the passage of radiant energy therethrough; and said dark window blocks both of said reference gas and said sample gas optical paths.

16. The gas analyzer of claim 15 wherein said chopper wheel is provided with sync marks and said circuit means includes means for generating reference gate, sample gate and dark gate signals.

17. The gas analyzer of claim 16 wherein said circuit means further includes a reference sample/hold circuit, a sample sample/hold circuit and a dark sample/hold circuit for receiving the output of said detector and said gate signals; said reference gate, said sample gate and said dark gate signals activating said reference, said sample and said dark sample/hold circuits, respectively, to detect and store for a predetermined period a detector reference signal, a detector sample signal and a detector dark signal, respectively.

18. The gas analyzer of claim 17 wherein the output of said reference and said dark sample/hold circuits is inputted to a first differential amplifier and the difference signal from said first differential amplifier is inputted to an automatic gain control circuit for maintaining said difference signal constant.

19. The gas analyzer of claim 18 wherein the outputs of said sample sample/hold circuit and said reference sample/hold circuit are inputted to a second differential amplifier where the outputs of said sample and said reference sample/hold circuits are subtracted from one another.

20. The gas analyzer of claim 19 wherein the output of said second differential amplifier is connected to means for indicating the concentration of a predetermined constituent gas contained in said sample gas.

21. The gas analyzer of claim 20 wherein said sample gas is breath gas expired from a patient and said predetermined constituent gas is carbon dioxide.

22. The gas analyzer of claim 1 wherein said sample gas cell comprises first and second substantially identical halves injection molded from a polymeric material and secured together.

23. The gas analyzer of claim 22 wherein each of said first and second halves includes half of said sample volume; sample window means comprising a transparent window bounding a portion of said sample volume; half of an inlet manifold; and half of an exhaust manifold.

24. The gas analyzer of claim 23 wherein a plurality of locator pins are disposed between said first and second halves, said locator pins extending into both of said first and second halves for accurately aligning the same during assembly.

25. The gas analyzer of claim 1 wherein the cross-sectional shape of said inlet manifold varies from a square at said inlet to an elongate rectangle at said sample volume, said rectangle being bounded by said window means.

26. The gas analyzer of claim 25 wherein said inlet manifold extends along a curve effecting approximately a 90° change in the direction of flow of the sample gas.

27. The gas analyzer of claim 1 wherein said cross-sectional shape of said exhaust manifold varies gradually from an elongate rectangle having a uniform width at the exit of said sample volume to a square at the outlet of said sample cell.

28. The gas analyzer of claim 27 wherein said inlet manifold extends along a curve effecting a first approximately 90° change in the direction of flow of the sample gas flowing into said sample volume; and said exhaust manifold extends along a curve effecting a second approximately 90° change in the direction of flow of the sample gas, such that said outlet and inlet are roughly parallel and sample gas flows in opposing directions in said inlet and outlet.

29. The gas analyzer of claim 1 wherein said source comprises a source of infrared energy and said detector means comprises an infrared sensitive lead selenide detector.

30. The gas analyzer of claim 1 wherein said gas cell is provided with a labyrinth seal surrounding the periphery of said gas cell for defining a mounting guide for said cell and reducing light leakage about the periphery of said cell.

31. The gas analyzer of claim 1 wherein the portion of said sample gas optical path extending through said sample gas volume is on the order of 1.0 mm.

32. The gas analyzer of claim 1 further including a negative cell disposed in said sample gas optical path ahead of said detector.

33. The gas analyzer of claim 32 wherein said negative cell comprises a plenum filled with a predetermined interfering gas found in the sample gas.

34. The gas analyzer of claim 33 wherein said analyzer is particularly adapted for measuring respired levels of carbon dioxide in breathing gases and said negative cell is filled with nitrous oxide.

* * * * *